United States Patent
Tu et al.

(10) Patent No.: US 6,306,133 B1
(45) Date of Patent: Oct. 23, 2001

(54) ABLATION CATHETER SYSTEM AND METHODS FOR REPAIRING A VALVULAR ANNULUS

(75) Inventors: Hosheng Tu; Cary Hata, both of Tustin, CA (US)

(73) Assignee: Quantum Cor Incorporated, Dana Point, CA (US)

( * ) Notice: Subject to any disclaimer, the term of this patent is extended or adjusted under 35 U.S.C. 154(b) by 0 days.

(21) Appl. No.: 09/410,902

(22) Filed: Oct. 2, 1999

(51) Int. Cl.[7] .................................................. A61B 18/18
(52) U.S. Cl. .............................. 606/41; 606/46; 606/47; 607/102
(58) Field of Search ............................... 606/41, 46, 47, 606/48, 49, 50; 607/101, 102

(56) References Cited

U.S. PATENT DOCUMENTS

| | | | |
|---|---|---|---|
| 3,656,185 | 4/1972 | Carpentier | 623/2 |
| 4,164,046 | 8/1979 | Cooley | 3/1.5 |
| 5,456,662 | 10/1995 | Edwards et al. | 604/22 |
| 5,546,954 | 8/1996 | Yamada | 128/735 |
| 5,674,279 | 10/1997 | Wright et al. | 623/2 |
| 5,779,669 | 7/1998 | Haissaguerre et al. | 604/95 |
| 5,916,213 | 6/1999 | Haissaguerre et al. | 606/41 |
| 5,931,811 | 8/1999 | Haissaguerre et al. | 604/95 |
| 6,047,700 | * 4/2000 | Eggers et al. | 606/41 |
| 6,056,744 | * 5/2000 | Edwards | 606/41 |

OTHER PUBLICATIONS

Gabriel Spera "The Next Wave in Minimally Invasive Surgery" in Medical Device & Diagnostic Industry pp. 36–44, Aug. 1998.

* cited by examiner

Primary Examiner—Linda C. M. Dvorak
Assistant Examiner—David Ruddy

(57) ABSTRACT

An ablation catheter system and methods for repairing an annular organ structure comprising high frequency ablation for the purposes of tightening and stabilizing a tissue. A catheter suitable for high frequency ablation comprises a flexible tissue-contactor means located at the distal tip section of a catheter shaft for contacting an inner wall of the annular organ structure, and a needle electrode means located at or within the flexible tissue-contactor means for penetrating into the tissue, wherein the needle electrode means is deployable out of the tissue-contactor means in a manner essentially perpendicular to a longitudinal axis of the catheter shaft.

10 Claims, 7 Drawing Sheets

ABLATION CATHETER SYSTEM AND METHODS FOR REPAIRING A VALVULAR ANNULUS

FIELD OF THE INVENTION

The present invention generally relates to systems and methods for applying electrical energy to a patient for medical purposes such as reducing and/or shriking a tissue mass. More particularly, the invention relates to an ablation catheter system that penetrates the tissue of a valvular annulus in order to tighten and stabilize an annular organ structure.

BACKGROUND OF THE INVENTION

The circulatory system consists of a heart and blood vessels. In its path through the heart, the blood encounters four valves. The valve on the right side that separates the right atrium from the right ventricle has three cusps and is called the tricuspid valve. It closes when the ventricle contracts during a phase known as systole and it opens when the ventricle relaxes, a phase known as diastole.

The pulmonary valve separates the right ventricle from the pulmonary artery. It opens during systole, to allow the blood to be pumped toward the lungs, and it closes in diastole to keep the blood from leaking back into the heart from the pulmonary artery. The pulmonary valve has three cusps, each one resembling a crescent and it is also known as a semi-lunar valve.

The mitral valve, so named because of its resemblance to a bishop's mitre, is in the left ventricle and it separates the left atrium from the ventricle. It opens during diastole to allow the blood stored in the atrium to pour into the ventricle, and it closes during systole to prevent blood from leaking back into the atrium. The mitral valve and the tricuspid valve differ significantly in anatomy. The annulus of mitral valve is somewhat D-shaped whereas the annulus of the tricuspid valve is more nearly circular.

The fourth valve is the aortic valve. It separates the left ventricle from the aorta. It has three semi-lunar cusps and it closely resembles the pulmonary valve. The aortic valve opens during systole allowing a stream of blood to enter the aorta and it closes in diastole to prevent any of the blood from leaking back into the left ventricle.

In a venous circulatory system, a venous valve is to prevent the venous blood from leaking back into the upstream side so that the venous blood can return to the heart and the lungs for blood oxygenating purposes.

Clinical experience has shown that repair of a valve, either a heart valve or a venous valve, produces better long-term results than does valve replacement. Valve replacement using a tissue valve suffers long-term calcification problems. On the other hand, anticoagulation medicine, such as heparin, is required for the life of a patient when a mechanical valve is used in valve replacement. The current technology for valve repair or valve replacement requires an expensive open-heart surgery that needs a prolonged period of recovery. A less invasive catheter-based valve repair technology becomes an unmet clinical challenge.

The effects of valvular dysfunction vary. Mitral regurgitation has more severe physiological consequences to the patient than does tricuspid valve regurgitation. In patients with valvular insufficiency it is an increasingly common surgical practice to retail the natural valve, and to attempt to correct the defects. Many of the defects are associated with dilation of the valve annulus. This dilation not only prevents competence of the valve but also results in distortion of the normal shape of the valve orifice or valve leaflets. Remodeling of the annulus is therefore central to most reconstructive procedures on the mitral valve.

As a part of the valve repair it is either necessary to diminish or constrict the involved segment of the annulus so that the leaflets may coapt correctly on closing, or to stabilize the annulus to prevent post-operative dilation from occurring. The current open-heart approach is by implantation of a prosthetic ring, such as a Cosgrove Ring or a Carpentier Ring, in the supra annular position. The purpose of the ring is to restrict and/or support the annulus to correct and/or prevent valvular insufficiency. In tricuspid valve repair, constriction of the annulus usually takes place in the posterior leaflet segment and in a small portion of the adjacent anterior leaflet.

Various prostheses have been described for use in conjunction with mitral or tricuspid valve repair. The ring developed by Dr. Alain Carpentier (U.S. Pat. No. 3,656,185) is rigid and flat. An open ring valve prosthesis as described in U.S. Pat. No. 4,164,046 comprises a uniquely shaped open ring valve prosthesis having a special velour exterior for effecting mitral and tricuspid annuloplasty. The fully flexible annuloplasty ring could only be shortened in the posterior segment by the placement of placating sutures. John Wright et al. in U.S. Pat. No. 5,674,279 discloses a suturing ring suitable for use on heart valve prosthetic devices for securing such devices in the heart or other annular tissue. All of the above valve repair or replacement requires an open-heart operation which is costly and exposes a patient to higher risk and longer recovery than a catheter-based less invasive procedure.

Moderate heat is known to tighten and shrink the collagen tissue as illustrated in U.S. Pat. No. 5,456,662 and U.S. Pat. No. 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, August 1998). Therefore, it becomes imperative to treat the inner walls of an annular organ structure of a heart valve, a valve leaflet, chordae tendinae, papillary muscles, and the like by shrinking/tightening techniques.

One method of reducing the size of tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment devices have an advantage because of the use of a therapeutic energy that is rapidly dissipated and reduced to a non-destructive level by conduction and convection, to other natural processes.

RF therapeutic protocol has been proven to be highly effective when used by electrophysiologists for the treatment of tachycardia; by neurosurgeons for the treatment of Parkinson's disease; by otolaryngologist for clearing airway obstruction and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the device-to-tissue contact site to obtain the desired temperature for treating a tissue.

Therefore, there is a clinical need to have a less invasive catheter-based approach for repairing an annular organ structure of a heart valve, a valve leaflet, chordae tendinae, papillary muscles, and the like by using high frequency energy for reducing and/or shrinking a tissue mass for tightening and stabilizing the dilated tissue adjacent a valvular annulus.

SUMMARY OF THE INVENTION

In general, it is an object of the present invention to provide a catheter system and methods for repairing an annular organ structure of a heart valve, an annular organ structure of a venous valve, a valve leaflet, chordae tendinae, papillary muscles, and the like.

It is another object of the present invention to provide a catheter system and methods by using high frequency current for tissue treatment or repairing.

It is still another object to provide an ablation catheter system that penetrates the tissue of a valvular annulus in order to tighten and stabilize an annular organ structure.

It is a preferred object to provide a flexible tissue-contactor means located at the distal tip section of a catheter shaft for contacting an inner wall of an annular organ structure, wherein the tissue-contactor means is deployable out of the at least one lumen by a tissue-contactor deployment mechanism at the handle and wherein the tissue-contactor means is preformed and/or preshaped to have an appropriate form and shape compatible with the inner wall of an annular organ structure.

It is another object of the invention to provide an ablation catheter shaft with a tip section having a needle electrode means for penetrating into a tissue, wherein the needle electrode means is deployable out of the catheter shaft in a manner essentially perpendicular to a longitudinal axis of the catheter shaft.

It is still another object of the present invention to provide a catheter system and methods for providing high frequency current energy to the tissue/organ at or adjacent a heart valve structure.

In one embodiment, a catheter system comprises a flexible catheter shaft having a distal tip section, a distal end, a proximal end, and at least one lumen extending between the distal end and the proximal end. A flexible tissue-contactor means is located at the distal tip section and is inside the at least one lumen of the catheter shaft for contacting an inner wall of an annular organ structure, wherein the tissue-contactor means is deployable out of the at least one lumen by a tissue-contactor deployment mechanism located at a handle. The tissue-contactor means is preformed to have an appropriate shape, form, and size compatible with and intimately fittable onto the inner wall of the annular organ structure. A needle electrode means is located at, around, or within the flexible tissue-contactor means for penetrating into a tissue, wherein the needle electrode means is deployable out of the tissue-contactor means in a manner essentially perpendicular to a longitudinal axis of the catheter shaft. A handle is attached to the proximal end of the catheter shaft, wherein the handle comprises the tissue-contactor deployment mechanism and an electrode deployment means for advancing the needle electrode means out of the tissue-contactor means. The catheter system also comprises a high frequency current generator, wherein an electrical conductor means for transmitting high frequency current to the needle electrode means is provided. The high frequency current may be selected from the group consisting of radiofrequency current, microwave current and ultrasound current.

In a preferred embodiment, the tissue-contactor means may be selected from The group consisting of a circular ring, a round mass, a D-shaped ring, a kidney-shaped ring, an oval ring, and the like that is compatible with the shape of the to-be-treated organ. The tissue-contactor means may be made of a biocompatible material selected from the group consisting of silicone, latex, polyurethane, fabric, and a combination thereof. Alternately, the tissue-contactor means may comprise a plurality of open channels for a fluid to pass from a proximal end of said tissue-contactor means to a distal end of said tissue-contactor means. The open channels may include macropores or micropores.

In another preferred embodiment, the annular organ structure of the present invention may be a valvular annulus of a cardiovascular valve selected from the group consisting of a mitral valve, a tricuspid valve, a pulmonary valve, an aortic valve, a venous valve, or other valvular organ structure. The needle electrode means may comprise a plurality of needle electrodes that are preshaped to be essentially perpendicular to a longitudinal axis of the catheter shaft when deployed and wherein the high frequency current is delivered to each of the plurality of needle electrodes in a current delivery mode selected from the group consisting of an individual mode, a pulsed mode, a sequential mode, and a simultaneous mode. The needle electrode means may be made of a material selected from the group consisting of platinum, iridium, gold, silver, stainless steel, tungsten, and Nitinol.

The catheter system further comprises a steering mechanism at the handle for controlling the deflection of the distal tip section of the catheter shaft. Usually a rotating ring or a push-pull plunger is employed in the steering mechanism. In another preferred embodiment, the steerable ablation catheter comprises a bi-directional deflection or multiple curve deflection of the tip section. One end of the steering wire is attached at certain point of the tip section of the catheter shaft. The other end is attached to the steering mechanism at the handle. The steering mechanism on a steerable catheter. or device is well known to an ordinary person who is skilled in the art.

In a particular embodiment, one conducting wire of the electrical conductor means that is soldered to one needle electrode passes through the lumen of the catheter shaft and an interior void of the handle and is thereafter soldered to a contact pin of the connector secured at a proximal end of the handle. Therefrom, the conducting wire is connected to an external high frequency current generator for delivery of high frequency current during ablation operations.

In an additional embodiment, the catheter system further comprises a temperature sensing means and/or a closed-loop temperature control mechanism for the needle electrode means having at least one temperature sensor at the tissue contact site of the electrode means. The location of the temperature sensing means is preferably located adjacent to a distal tip of the needle electrode means.

In one embodiment, a method for operating a catheter system for repairing a valvular annulus, the method comprises (a) percutaneously introducing the catheter system through a blood vessel to a valvular annulus, wherein the catheter system comprises a flexible catheter shaft having a distal tip section, a distal end, a proximal end, and at least one lumen extending between the distal end and the proximal end; a flexible tissue-contactor means located at the distal tip section and inside the at least one lumen of the catheter shaft for contacting an inner wall of an annular organ structure, wherein the tissue-contactor means is deployable out of the at least one lumen by a tissue-contactor deployment mechanism and is preformed to have an appropriate shape compatible with the inner wall of the annular organ structure; a needle electrode means located at or within the flexible tissue-contactor means for penetrating into a tissue, wherein the needle electrode means is deployable out of the tissue-contactor means in a manner essentially perpendicular to a longitudinal axis of the catheter shaft; a handle attached to the proximal end of the catheter shaft, wherein the handle comprises the tissue-contactor deployment mechanism and an electrode deployment means for advancing the needle electrode means out of the tissue-contactor means; and a high frequency current generator; wherein an electrical conductor means for transmitting high frequency current to the needle electrode means is provided; (b) positioning the tissue-contactor means of the catheter shaft on the inner wall of the valvular annulus; (c) advancing the needle electrode means for penetrating the needle electrode means into a tissue of the valvular annulus; and (d) applying high frequency current through the electrical conductor means to the needle electrode means for repairing a valvular annulus.

In another embodiment, a method for operating a catheter system for repairing a tissue of a heart valve structure, the method comprises (a) percutaneously introducing the catheter system through a blood vessel to the tissue of the heart valve, wherein the catheter system comprises a flexible catheter shaft having a distal tip section, a distal end, a proximal end, and at least one lumen extending between the distal end and the proximal end; an electrode means located at the distal tip section of the catheter shaft for contacting the tissue of the heart valve; a handle attached to the proximal end of the catheter shaft, wherein the handle has a cavity; and a high frequency current generator, wherein an electrical conductor means for transmitting high frequency current to the electrode means is provided; (b) positioning the electrode means of the catheter system at the tissue of the heart valve; (c) applying high frequency current through the electrical conductor means to the electrode means for repairing the heart valve.

The catheter system of the present invention has several significant advantages over known catheters or ablation techniques for repairing an annular organ structure of a heart valve, a valve leaflet, chordae tendinae, papillary muscles, venous valve, and the like. In particular, the ablation catheter of this invention by using high frequency current energy for reducing and/or shrinking a tissue mass may tighten and stabilize the dilated tissue at or adjacent a valvular annulus.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
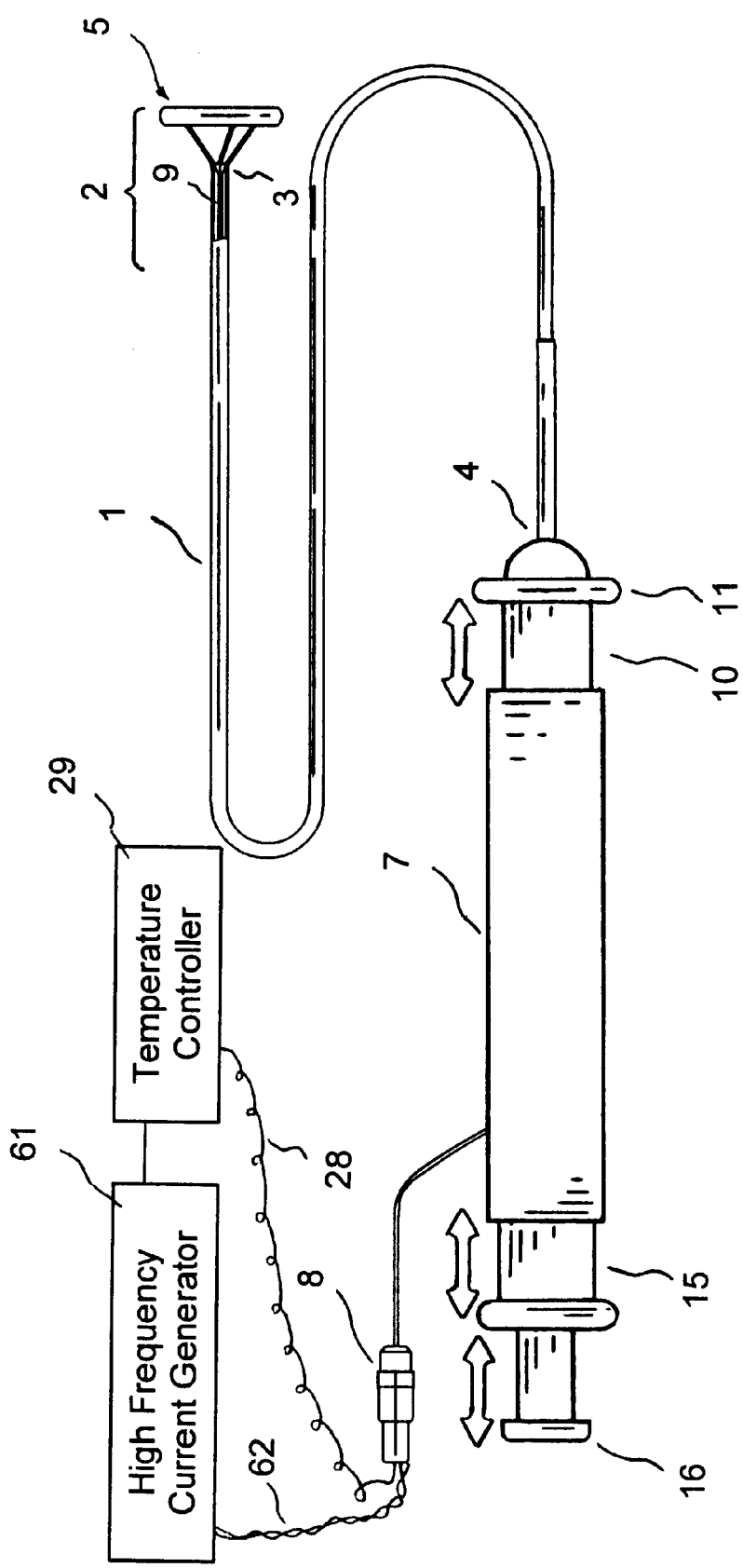
FIG. 1 is an overall view of a catheter system having a flexible tissue-contactor means and a needle electrode means at its distal tip section constructed in accordance with the principles of the present invention.

The following descriptions of the preferred embodiment of the invention are exemplary, rather than limiting, and many variations and modifications are within the scope of the invention. FIG. 1 shows an overall view of a catheter system having a flexible tissue-contactor means and a needle electrode means at its distal tip section constructed in accordance with the principles of the present invention. A catheter system constructed in accordance with the principles of the present invention comprises a flexible catheter shaft 1 having a distal tip section 2, a distal end 3, a proximal end 4, and at least one lumen 14 extending therebetween. The catheter system comprises a flexible, relatively semi-rigid tissue-contactor means 5 located at the distal tip section 2 and inside the at least one lumen 14 of said catheter shaft 1 for contacting an inner wall 51 of an annular organ structure 52 when deployed. The tissue-contactor means 5 is deployable out of the at least one lumen 14 by a tissue-contactor deployment mechanism 15 located at a handle 7. The tissue-contactor means 5 is preformed to have an appropriate shape compatible with the inner wall 51 of the annular organ structure 52. The tissue-contactor means 5 may be selected from the group consisting of a circular ring, a D-shaped ring, a kidney-shaped ring, an oval ring, and other round-shaped mass.

A handle 7 is attached to the proximal end 4 of the catheter shaft 1. The handle comprises the tissue-contactor deployment mechanism 15 and an electrode deployment means 16 for advancing a needle electrode means 9 out of the tissue-contactor means 5.

A connector 8 secured at the proximal end of the catheter system, is part of the handle section 7. The handle has one optional steering mechanism 10. The steering mechanism 10 is to deflect the distal tip section 2 of the catheter shaft 1 for catheter maneuvering and positioning. By pushing forward the front plunger 11 of the handle 7, the distal tip section 2 of the catheter shaft deflects to one direction. By pulling back the front plunger 11, the tip section returns to its neutral position. In another embodiment, the steering mechanism 10 at the handle 7 comprises means for providing a plurality of deflectable curves on the distal tip section 2 of the catheter shaft 1.

The catheter system also comprises a high frequency current generator 61, wherein an electrical conductor means 62 for transmitting high frequency current to the needle electrode means 9 is provided.

Figure 2:
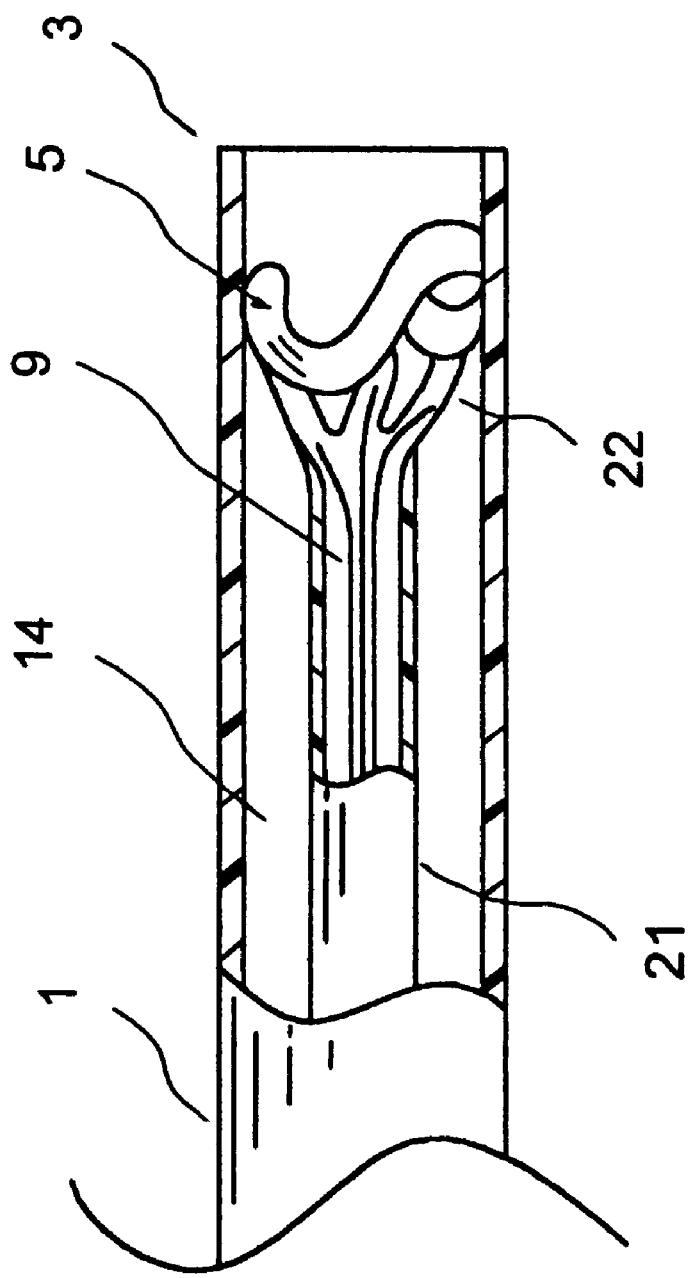
FIG. 2 is a close-up view of the distal tip section of the catheter system comprising a retracted tissue-contactor means and a retracted needle electrode means at a non-deployed state.

FIG. 2 shows a close-up view of the distal tip section 2 of the catheter system comprising a retracted tissue-contactor means 5 and a retracted needle electrode means 9 at a non-deployed state. Both the tissue-contactor means and the needle electrode means are retractable to stay within the at least one lumen 14. This non-deployed state is used for a catheter to enter into and to withdraw from the body of a patient. The tissue-contactor means is preformed and flexible enough so that it can easily retracted into the catheter lumen 14. The tissue-contactor means 5 may be made of a biocompatible material selected from the group consisting of silicone, latex, polyurethane, fabric, and a combination thereof. Reinforced substrate, such as mesh, wire, fiber, and the like, may be added to the tissue-contactor means 5 to make the tissue-contactor means semi-rigid so that when it is deployed, adequate pressure is exerted to the surrounding tissue for stabilizing its placement.

The catheter system comprises a needle electrode means 9 located at or within the flexible tissue-contactor means 5 for penetrating into a tissue, such as an inner wall 51, wherein the needle electrode means 9 is deployable out of the tissue-contactor means 5 in a manner essentially perpendicular to a longitudinal axis of the catheter shaft 1 when the needle electrode means is deployed. In another preferred embodiment, the angle of the needle electrode against a tissue may be any suitable angle from 30 degrees to 150 degrees in reference to a longitudinal axis of the catheter shaft for effective tissue penetration.

The needle electrode means 9 may comprise a plurality of needle electrodes 9A, 9B, 9C that are preshaped to be essentially perpendicular to a longitudinal axis of the catheter shaft 1 when deployed. The high frequency current may be delivered to each of the plurality of needle electrodes 9A, 9B, 9C in a current delivery mode selected from the group consisting of individual delivery mode, pulsed delivery mode, sequential delivery mode, and simultaneous delivery mode.

The needle electrode means 9 may be made of a material selected from the group consisting of platinum, iridium, gold, silver, stainless steel, tungsten, Nitinol, and other conducting material. The needle electrode means 9 is connected to an electrode deployment means 16 at the handle 7 for advancing one or more needles of the needle electrode means 9 out of the tissue-contactor means 5. This electrode deployment means may include various deployment modes of a single needle electrode deployment, a plurality of needle electrodes deployment or all needle electrodes simultaneous deployment.

The tissue-contactor means 5 in this invention is defined as a flexible semi-rigid element adapted for contacting an inner wall of an annular organ structure of a patient and is also preformed to have an appropriate shape compatible with the inner wall of the annular organ structure. The tissue-contactor means may comprise a plurality of grooves or internal channels 25 so that a needle electrode of the needle electrode means is able to deploy out of and retract into the tissue contactor means with minimal frictional resistance.

Figure 3:
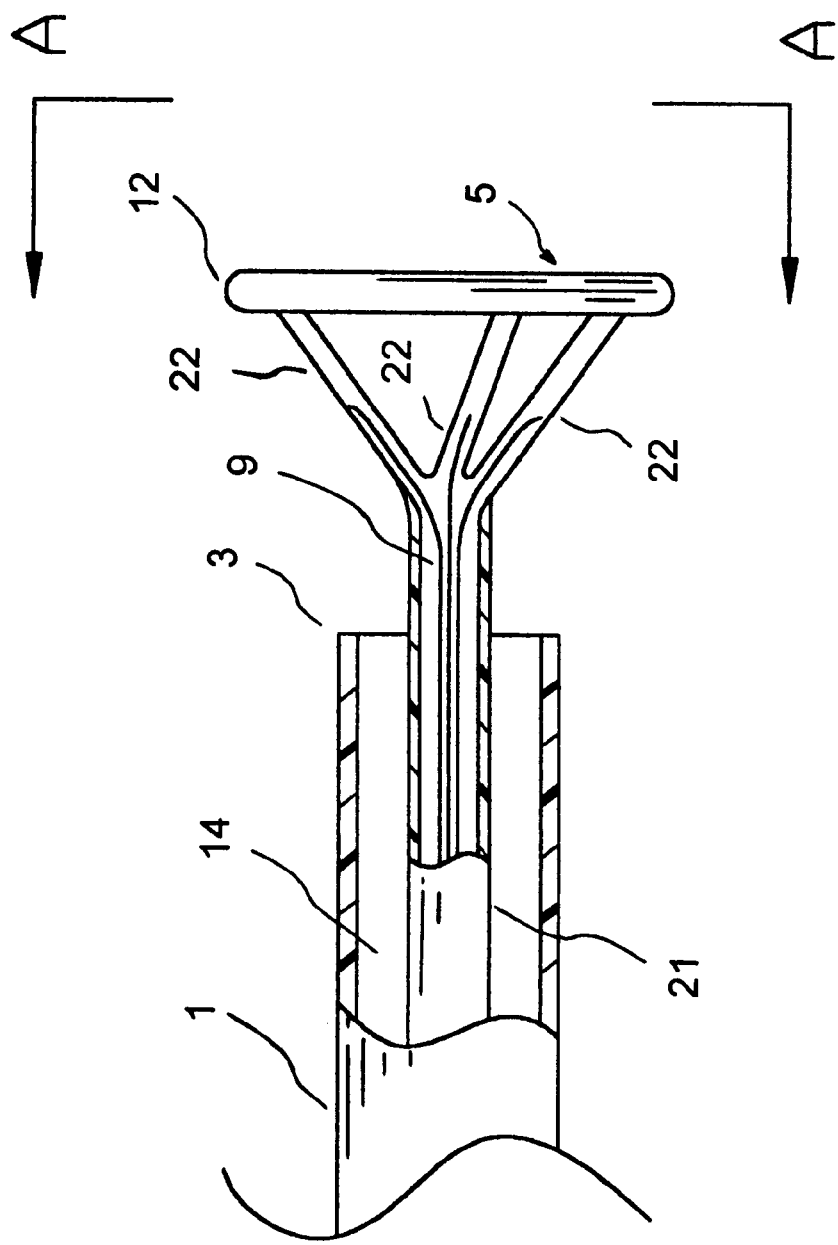
FIG. 3 is a close-up view of the distal tip section of the catheter system comprising a deployed tissue-contactor means and a retracted needle electrode means.

FIG. 3 shows a close-up view of the distal tip section 2 of the catheter system comprising a deployed tissue-contactor means 5 and a retracted needle electrode means 9. The outer diameter of the deployed tissue-contactor means 5 is optionally larger than the outer diameter of the catheter shaft 1 so that the outer rim 12 of the deployed tissue-contactor means may stably stay on the inner wall of the annular organ structure. A supporting member 21 along with a plurality of auxiliary supporting members 22 on the distal end of the supporting member 21 form a connecting means for connecting the tissue-contactor means 5 to the tissue-contactor deployment mechanism 15 that is located on the handle 7.

The supporting member 21 and the auxiliary supporting members 22 are located within the at least one lumen 14 and have torque transmittable property and adequate rigidity to deploy the tissue-contactor means 5.

The needle electrode is preferably made of conductive material, while the surfaces of the catheter shaft 1, conducting wires 62, the supporting member 21, and the auxiliary supporting members 22, are preferably covered with an insulating material or insulated.

Figure 4:
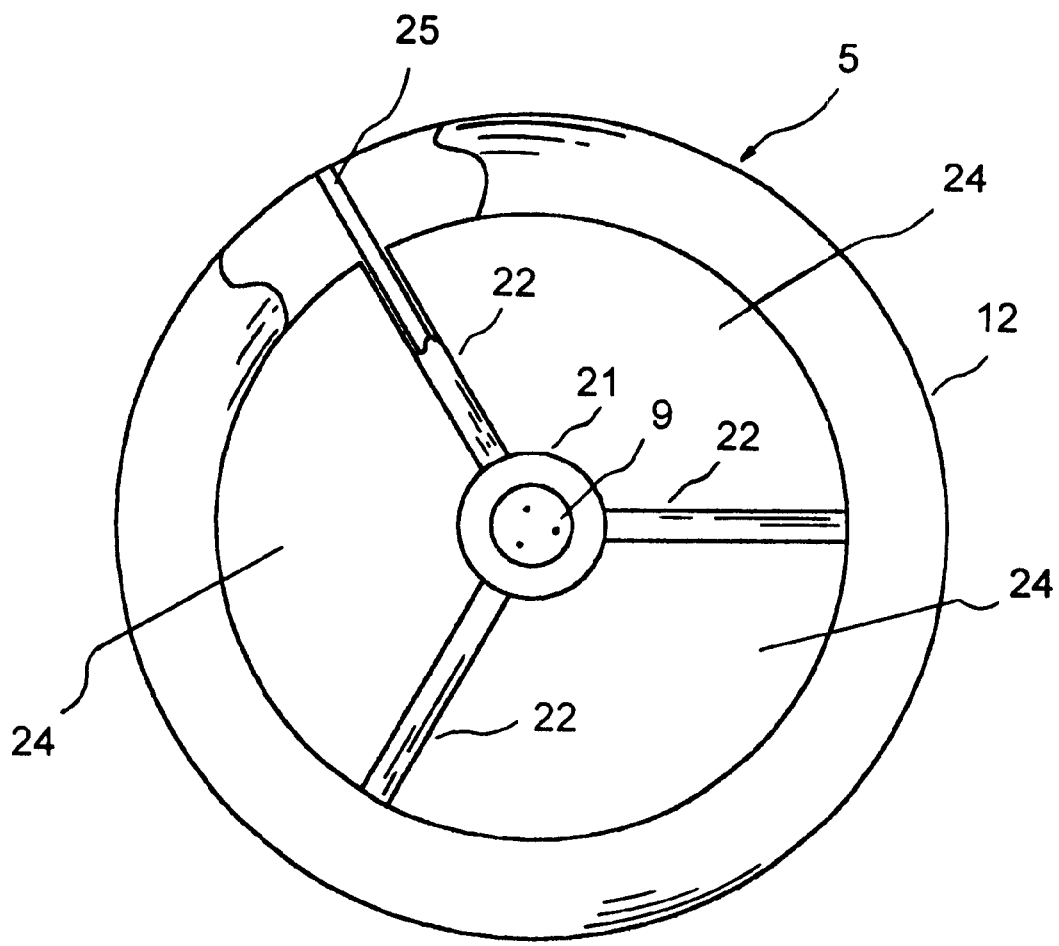
FIG. 4 is a front cross-sectional view, section A—A of FIG. 3, of the distal tip section of a catheter system comprising a deployed tissue-contactor means.

FIG. 4 shows a front cross-sectional view, section A—A of FIG. 3, of the distal tip section of a catheter system comprising a deployed tissue-contactor means 5. The tissue-contactor means 5 may comprise a plurality of open channels 24, pores and the like for a fluid or blood to pass from a proximal end of the tissue-contactor means 5 to a distal end of the tissue-contactor means.

Figure 5:
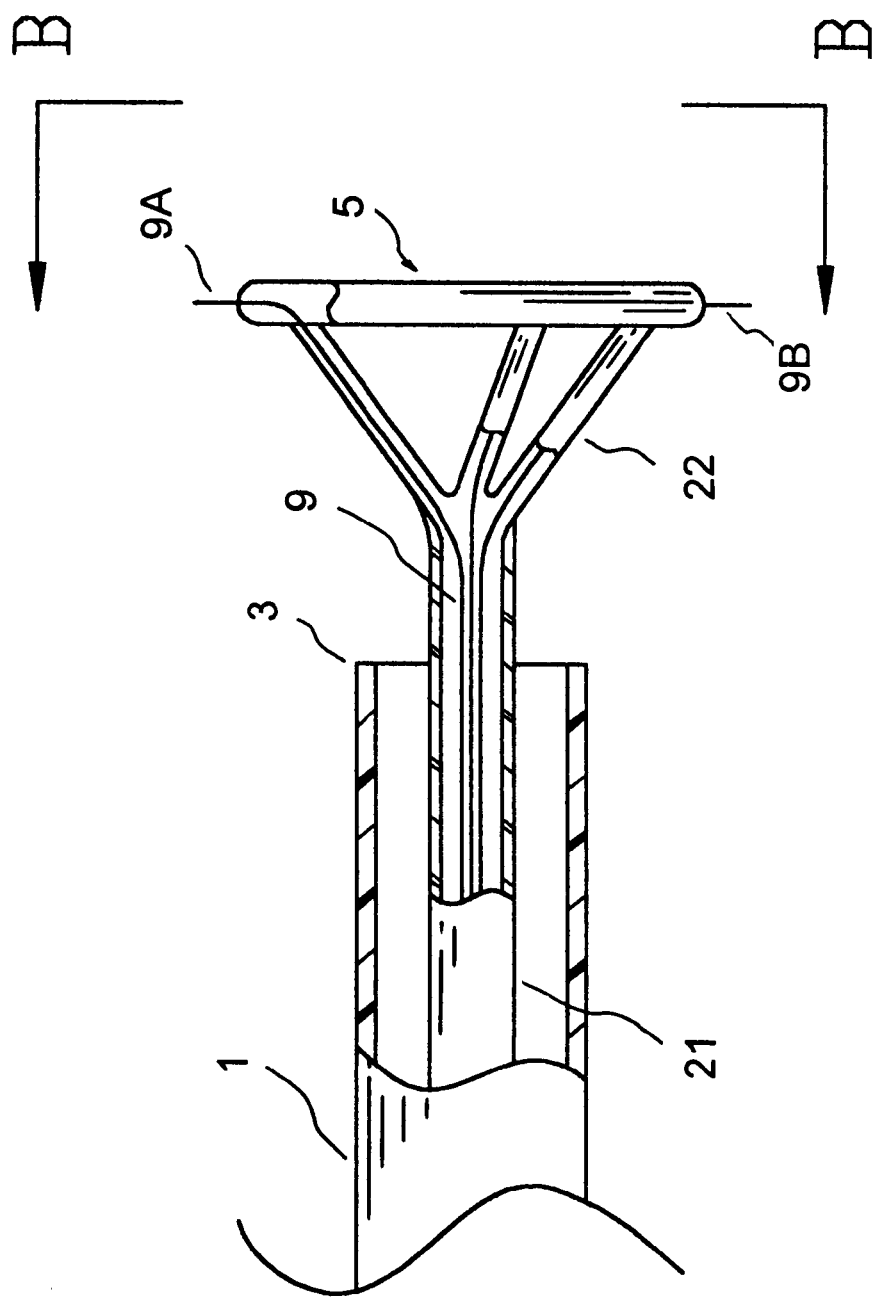
FIG. 5 is a close-up view of the distal tip section of the catheter system comprising a deployed tissue-contactor means and a deployed needle electrode means at a fully deployed state.

FIG. 5 shows a close-up view of the distal tip section 2 of the catheter system comprising a deployed tissue-contactor means 5 and a deployed needle electrode means 9 at a fully deployed state. The fully deployed state is used for delivery of high frequency current energy to the needle electrode means 9 and subsequently to the contact tissue for repairing the annular organ structure. The delivery of high frequency current to each of the needle electrodes may go through a splitter or other mechanism. The needle electrode means is preformed so that when deployed, the needle electrodes are in a manner essentially perpendicular to a longitudinal axis of the catheter shaft 1 for effective thermal therapy.

Figure 6:
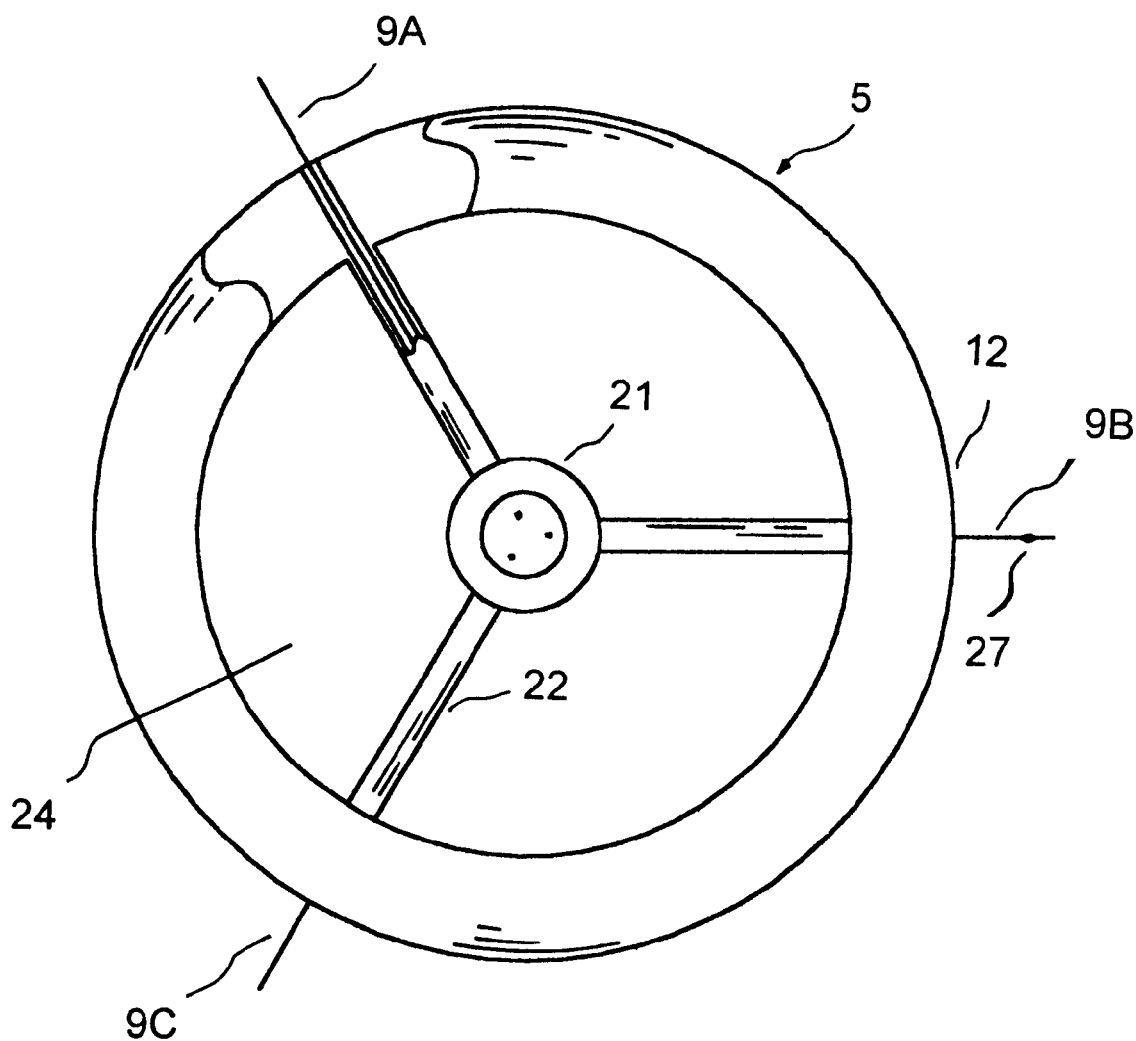
FIG. 6 is a front cross-sectional view, section B—B of FIG. 5, of the distal tip section of a catheter system comprising a deployed tissue-contactor means and a deployed needle electrode means.

FIG. 6 shows a front cross-sectional view, section B—B of FIG. 5, of the distal tip section 2 of a catheter system comprising a deployed tissue-contactor means 5 and a deployed needle electrode means 9. The tips of the needle electrodes 9A, 9B, 9C extend out of the rim 12 of the tissue-contactor means 5 and penetrate into a tissue for energy delivery.

Figure 7:
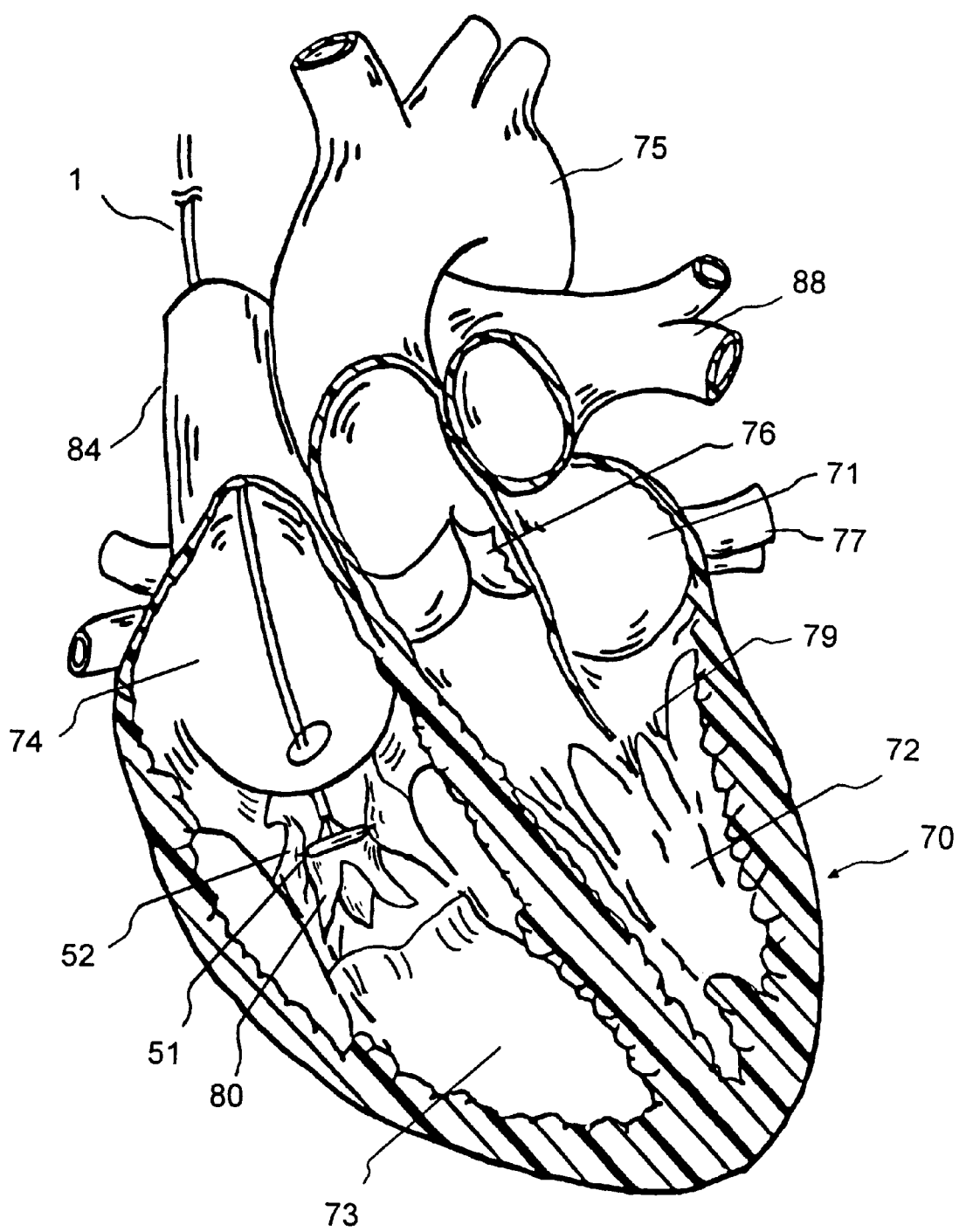
FIG. 7 is a simulated view of the catheter system of the present invention in contact with the tissue of an annular organ structure.

FIG. 7 shows a simulated view of the catheter system of the present invention in contact with the tissue of an annular organ structure 52. The heart 70 has a left atrium 71, a left ventricle 72, a right ventricle 73, and a right atrium 74. Aorta 75 connects with the left ventricle 72 and contains an aorta valve 76. Pulmonary artery 77 connects with the right ventricle 73 through a pulmonary valve. Left atrium 71 communicates with the left ventricle 72 through a mitral valve 79. The right atrium 74 communicates with the right ventricle 73 through a tricuspid valve 80. Oxygenated blood is returned to the heat 70 via pulmonary veins 88. In a perspective illustration, a catheter is inserted into the right atrium 74 and is positioned on the inner wall 51 of the tricuspid valve 80. The leaflets of the tricuspid valve 80 open toward the ventricle side. Blood returned from the superior vena cava 84 and the inferior vena cava flows into the right atrium 74. Subsequently, blood flows from the right atrium 74 to the right ventricle 73 through the tricuspid valve 80. Therefore, the tissue-contactor means 5 of the catheter shaft 1 does not interfere with the leaflet movement during the proposed less invasive thermal therapy of the invention.

In a preferred embodiment, a method for operating a catheter system of the present invention for repairing a valvular annulus, the method comprises (a) percutaneously introducing the catheter system through a blood vessel to a valvular annulus; (b) positioning the tissue-contactor means of the catheter shaft on the inner wall of the valvular annulus; (c) advancing the needle electrode means for penetrating the needle electrode means into a tissue of the valvular annulus; and (d) applying high frequency current through the electrical conductor means to the needle electrode means for repairing a valvular annulus.

In another preferred embodiment, a method for operating a catheter system for repairing a tissue of a heart valve, the catheter system comprises a flexible catheter shaft having a distal tip section, a distal end, a proximal end, and at least one lumen extending between the distal end and the proximal end; an electrode means located at the distal tip section of the catheter shaft for contacting the tissue of the heart valve; a handle attached to the proximal end of the catheter shaft, wherein the handle has a cavity; and a high frequency current generator, wherein an electrical conductor means for transmitting high frequency current to said electrode means is provided. The method comprises (a) percutaneously introducing the catheter system through a blood vessel to the tissue of the heart valve; (b) positioning the electrode means of the catheter system at the tissue of the heart valve; and (c) applying high frequency current through the electrical conductor means to the electrode means for repairing the heart valve.

The tissue of the heart valve in the procedures may be selected from the group consisting of valvular annulus, chordae tendinae, valve leaflet, and papillary muscles. The high frequency current in the procedures may be selected from the group consisting of radiofrequency current, microwave current, and ultrasound current.

A temperature sensor 27, either a thermocouple type or a thermister type, is constructed at the proximity of the needle electrode 9B (shown in FIG. 6) to measure the tissue contact temperature when high frequency energy is delivered. A temperature sensing wire 28 from the thermocouple or thermister is connected to one of the contact pins of the connector 8 and externally connected to a transducer and to a temperature controller 29. The temperature reading is thereafter relayed to a closed-loop control mechanism to adjust the high frequency energy output. The high frequency energy delivered is thus controlled by the temperature sensor reading or by a pre-programmed control algorithm.

From the foregoing, it should now be appreciated that an improved catheter system having needle electrode means and high frequency current energy for penetrating the tissue of a valvular annulus in order to tighten and stabilize an annular organ structure has been disclosed for repairing an annular organ structure of a heart valve, an annular organ structure of a venous valve, a valve leaflet, chordae tendinae, papillary muscles, and the like. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:
a flexible catheter shaft having a distal tip section, a distal end, a proximal end, and at least one lumen extending between the distal end and the proximal end;
a flexible tissue-contactor ring located at the distal tip section and inside the at least one lumen of said catheter shaft for contacting an inner wall of an annular organ structure, wherein said tissue-contactor ring is deployable out of the at least one lumen by a tissue-contactor deployment mechanism and is preformed to have an appropriate shape compatible with said inner wall of the annular organ structure, wherein said appropriate shape is a circular shape, a D-shape, a kidney shape, or an oval shape;
a needle electrode element located at or within the flexible tissue-contactor ring for penetrating into a tissue, wherein the needle electrode element is deployable out of the tissue-contactor ring in a manner essentially perpendicular to a longitudinal axis of the catheter shaft;
a handle attached to the proximal end of the catheter shaft, wherein the handle comprises the tissue-contactor deployment mechanism and an electrode deployment means for advancing the needle electrode out of said tissue-contactor ring; and
a high frequency current generator, wherein an electrical conductor means for transmiting high frequency current to said needle electrode element is provided.

2. The catheter system of claim 1, wherein the tissue-contactor ring is made of a biocompatible material selected from the group consisting of silicone, latex, polyurethane, fabric, and a combination thereof.

3. The catheter system of claim 1, wherein the tissue-contactor ring comprises a plurality of open channels for a fluid to pass from a proximal end of said tissue-contactor ring to a distal end of said tissue-contactor ring.

4. The catheter system of claim 1, wherein the annular organ structure is a valvular annulus of a cardiovascular valve selected from the group consisting of a mitral valve, a tricuspid valve, a pulmonary valve, an aortic valve, and a venous valve.

5. A method for operating a catheter system for repairing a valvular annulus, the catheter system comprising a flexible catheter shaft having a distal tip section, a distal end, a proximal end, and at least one lumen extending between the distal end and the proximal end; a flexible tissue-contactor ring located at the distal tip section and inside the at least one lumen of said catheter shaft for contacting an inner wall of an annular organ structure, wherein said tissue-contactor ring is deployable out of the at least one lumen by a tissue-contactor deployment mechanism and is preformed to have an appropriate shape compatible with said inner wall of the annular organ structure; a needle electrode element located at or within the flexible tissue-contactor ring for penetrating into a tissue, wherein the needle electrode element is deployable out of the tissue-contactor ring in a manner essentially perpendicular to a longitudinal axis of the catheter shaft; a handle attached to the proximal end of the catheter shaft, wherein the handle comprises the tissue-contactor deployment mechanism and an electrode deployment means for advancing the needle electrode element out of said tissue-contactor ring; and a high frequency current generator, wherein an electrical conductor means for transmitting high frequency current to said needle electrode element is provided;

the method comprising:
(a) percutaneously introducing the catheter system through a blood vessel to a valvular annulus;
(b) positioning the tissue-contactor ring of the catheter shaft on the inner wall of the valvular annulus;
(c) advancing the needle electrode element for penetrating the needle electrode element into a tissue of the valvular annulus; and
(d) applying high frequency current through the electrical conductor means to the needle electrode element for repairing a valvular annulus.

6. The method for operating a catheter system for repairing a valvular annulus of claim 5, wherein the tissue-contactor ring comprises a plurality of open channels for blood to pass through said tissue-contactor ring.

7. The method for operating a catheter system for repairing a valvular annulus of claim 5, wherein the valvular annulus is selected from the group consisting of a mitral valve, a tricuspid valve, a pulmonary valve, an aortic valve, and a venous valve.

8. The method for operating a catheter system for repairing a valvular annulus of claim 5, wherein the needle electrode element comprises a plurality of needle electrodes that are preshaped to be essentially perpendicular to a longitudinal axis of the catheter shaft when deployed and wherein the high frequency current is delivered to each of said plurality of needle electrodes in a mode selected from the group consisting of individual mode, pulsed mode, sequential mode, and simultaneous mode.

9. The method for operating a catheter system for repairing a valvular annulus of claim 5, wherein the high frequency current is selected from the group consisting of radiofrequency current, microwave current and ultrasound current.

10. The method for operating a catheter system for repairing a valvular annulus of claim 5, wherein the tissue-contactor ring is made of a biocompatible material selected from the group consisting of silicone, latex, polyurethane, fabric, and a combination thereof.

* * * * *